United States Patent
Ford et al.

(10) Patent No.: US 7,682,152 B2
(45) Date of Patent: Mar. 23, 2010

(54) FORCE DISTRIBUTING DENTAL IMPLANT ASSEMBLY

(76) Inventors: Christopher W. Ford, 4340 Lahring Rd., Holly, MI (US) 48442; Boney A. Mathew, 7167 Blue Water Dr., Clarkston, MI (US) 48348

( * ) Notice: Subject to any disclaimer, the term of this patent is extended or adjusted under 35 U.S.C. 154(b) by 75 days.

(21) Appl. No.: 11/874,515

(22) Filed: Oct. 18, 2007

(65) Prior Publication Data
US 2008/0261177 A1    Oct. 23, 2008

Related U.S. Application Data

(63) Continuation-in-part of application No. 11/312,996, filed on Dec. 20, 2005, now abandoned.

(60) Provisional application No. 60/858,772, filed on Nov. 13, 2006.

(51) Int. Cl.
*A61C 8/00* (2006.01)
(52) U.S. Cl. .............................. 433/174; 433/169
(58) Field of Classification Search ............... 433/170, 433/171, 172, 218, 219, 220, 221, 22, 223, 433/222, 173, 174, 175, 182, 183, 201.1, 433/202.1, 169
See application file for complete search history.

(56) References Cited

U.S. PATENT DOCUMENTS

| | | |
|---|---|---|
| 3,579,831 A | 5/1971 | Stevens et al. |
| 3,628,248 A | 12/1971 | Kroder et al. |
| 3,740,851 A | 6/1973 | Weissman |
| 3,849,887 A | 11/1974 | Brainin |
| 3,934,347 A | 1/1976 | Lash et al. |
| 3,955,280 A | 5/1976 | Sneer |
| 4,051,598 A | 10/1977 | Sneer |
| 4,202,101 A | 5/1980 | Weissman |
| 4,252,525 A | 2/1981 | Child |
| 4,259,072 A | 3/1981 | Hirabayashi et al. |
| 4,281,992 A | 8/1981 | Colpitts et al. |
| 4,396,377 A | 8/1983 | Roemer et al. |
| 4,449,937 A | 5/1984 | Weissman |
| 4,536,158 A | 8/1985 | Bruins et al. |
| 4,547,327 A | 10/1985 | Bruins et al. |
| 4,622,010 A | 11/1986 | Koch |
| 4,713,003 A | 12/1987 | Symington et al. |
| 4,731,085 A | 3/1988 | Koch |
| 4,744,755 A | 5/1988 | Ross |
| 4,812,120 A | 3/1989 | Flanagan et al. |
| 4,881,897 A | 11/1989 | Franek et al. |
| 4,886,456 A | 12/1989 | Ross |
| 4,957,437 A | 9/1990 | Shimura et al. |
| 4,993,950 A | 2/1991 | Mensor, Jr. |
| 5,002,488 A | 3/1991 | Homsy |

(Continued)

*Primary Examiner*—Ralph A Lewis
*Assistant Examiner*—Eric Rosen
(74) *Attorney, Agent, or Firm*—Dickinson Wright PLLC

(57) ABSTRACT

A dental implant assembly (20) including a core body (40, 140, 240, 340, 440) for engaging a tooth-replicating device (52). The core body (40, 140, 240, 340, 440) is disposed in an anchor body (24, 124, 224, 424), and a screw cap body (58) is disposed about the outer attachment surface (30, 130, 230, 430) of the anchor body (24, 124, 224, 424). The screw cap body (58) engages the bone (22) of a person to support the dental implant assembly (20) and holds the core body (40, 140, 240, 340, 440) and the anchor body (24, 124, 224, 424) together.

18 Claims, 4 Drawing Sheets

U.S. PATENT DOCUMENTS

| | | | |
|---|---|---|---|
| 5,006,068 A | 4/1991 | Lee et al. | |
| 5,052,931 A | 10/1991 | Kirsch | |
| 5,062,798 A | 11/1991 | Tsuge et al. | |
| 5,106,299 A * | 4/1992 | Ghalili | 433/172 |
| 5,174,755 A | 12/1992 | Fukuda | |
| 5,180,303 A | 1/1993 | Hornburg et al. | |
| 5,213,500 A | 5/1993 | Salazar et al. | |
| 5,269,686 A | 12/1993 | James | |
| 5,397,235 A | 3/1995 | Elia | |
| 5,437,551 A * | 8/1995 | Chalifoux | 433/173 |
| 5,453,007 A | 9/1995 | Wagher | |
| 5,509,804 A * | 4/1996 | Arzt | 433/169 |
| 5,558,517 A | 9/1996 | Shalaby et al. | |
| 5,564,929 A | 10/1996 | Alpert | |
| 5,573,401 A | 11/1996 | Davidson et al. | |
| 5,584,693 A | 12/1996 | Nishihara | |
| 5,678,994 A | 10/1997 | Morehead | |
| 5,759,033 A | 6/1998 | Elia | |
| 5,879,161 A | 3/1999 | Lazzara | |
| 5,897,318 A | 4/1999 | Badoz | |
| 5,947,734 A | 9/1999 | Hanel | |
| 5,954,505 A * | 9/1999 | Ford | 433/177 |
| 5,964,592 A | 10/1999 | Hites et al. | |
| 6,183,255 B1 | 2/2001 | Oshida | |
| 6,193,516 B1 | 2/2001 | Story | |
| 6,250,922 B1 * | 6/2001 | Bassett et al. | 433/172 |
| 6,287,116 B2 | 9/2001 | Lazzara | |
| 6,299,448 B1 | 10/2001 | Zdrahala et al. | |
| 6,431,868 B2 | 8/2002 | Story | |
| 6,450,812 B1 | 9/2002 | Laster et al. | |
| 6,638,069 B2 | 10/2003 | Hagenbuch et al. | |
| 6,805,556 B2 * | 10/2004 | Kiyomi | 433/168.1 |
| 6,840,770 B2 | 1/2005 | McDevitt | |
| 6,863,530 B2 | 3/2005 | McDevitt | |
| 6,974,322 B2 | 12/2005 | May et al. | |
| 7,004,976 B2 | 2/2006 | Ornberg et al. | |
| 7,094,418 B2 | 8/2006 | Chudzik et al. | |
| 3,797,113 A1 | 10/2007 | Brainin | |
| 2001/0000486 A1 | 4/2001 | Story | |
| 2001/0051832 A1 | 12/2001 | Bakker et al. | |
| 2002/0031747 A1 | 3/2002 | Laster et al. | |
| 2002/0031749 A1 | 3/2002 | Morgan | |
| 2002/0076673 A1 | 6/2002 | Wagner et al. | |
| 2002/0177103 A1 | 11/2002 | Pelak | |
| 2004/0029075 A1 | 2/2004 | Peltier et al. | |
| 2004/0053195 A1 | 3/2004 | Blacklock | |
| 2004/0209228 A1 | 10/2004 | Ilan | |
| 2005/0037319 A1 * | 2/2005 | Bulard et al. | 433/173 |
| 2006/0014120 A1 | 1/2006 | Sapian | |
| 2007/0037123 A1 * | 2/2007 | Mansueto et al. | 433/173 |
| 2007/0054241 A1 * | 3/2007 | Kim | 433/173 |

* cited by examiner

US 7,682,152 B2

FORCE DISTRIBUTING DENTAL IMPLANT ASSEMBLY

CROSS REFERENCE TO RELATED APPLICATION

This application is a continuation-in-part and claims priority to co-pending U.S. application Ser. No. 11/312,996, filed Dec. 20, 2005, and U.S. provisional patent application No. 60/858,772, filed Nov. 10, 2006.

BACKGROUND OF THE INVENTION

1. Field of the Invention

The subject invention relates to a dental implant assembly that can be attached to a bone of a person.

2. Description of the Prior Art

Dental implants of numerous and varying designs have existed for many years. Many prior art dental implants include tooth-replicating devices that are attached inside a patient's mouth to replace lost teeth and to restore natural dental function. Force distributing dental implants were designed to improve the durability and life of implants by allowing the tooth-replicating device to move relative to the anchor, which is engaged with the patient's bone.

Such a force distributing dental implant assembly is disclosed in U.S. Pat. No. 5,954,505, issued on Sep. 21, 1999, in the name of one of the inventors herein. The force distributing assembly of the '505 patent includes an anchor body having an anchor pocket and an outer attachment surface for engaging the bone. The assembly also includes a core body disposed in the anchor pocket for engaging a tooth-replicating device. The core body and the anchor body are held together by a threaded fixation means engaging the inner wall of the anchor pocket.

SUMMARY OF THE INVENTION AND ADVANTAGES

The invention relates to such a force distributing dental implant assembly including an anchor body having an outer attachment surface for engaging the bone of a person and an inner wall defining an anchor pocket. A core body is disposed in the anchor pocket for engaging a tooth-replicating device. The invention is distinguished by a screw cap body disposed about the outer attachment surface of the anchor body for engaging the bone and for holding the core body and the anchor body together.

Typical force distributing dental implant assemblies require a reinforced anchor and an additional part to hold the core body and the anchor body together. The present invention allows for a screw cap body to engage the bone and hold the anchor body and core body together. The screw cap body functions to hold the dental implant assembly together and supports the force distributing implant assembly, thereby allowing the anchor body to be of a cheaper, weaker material.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Figure 1:
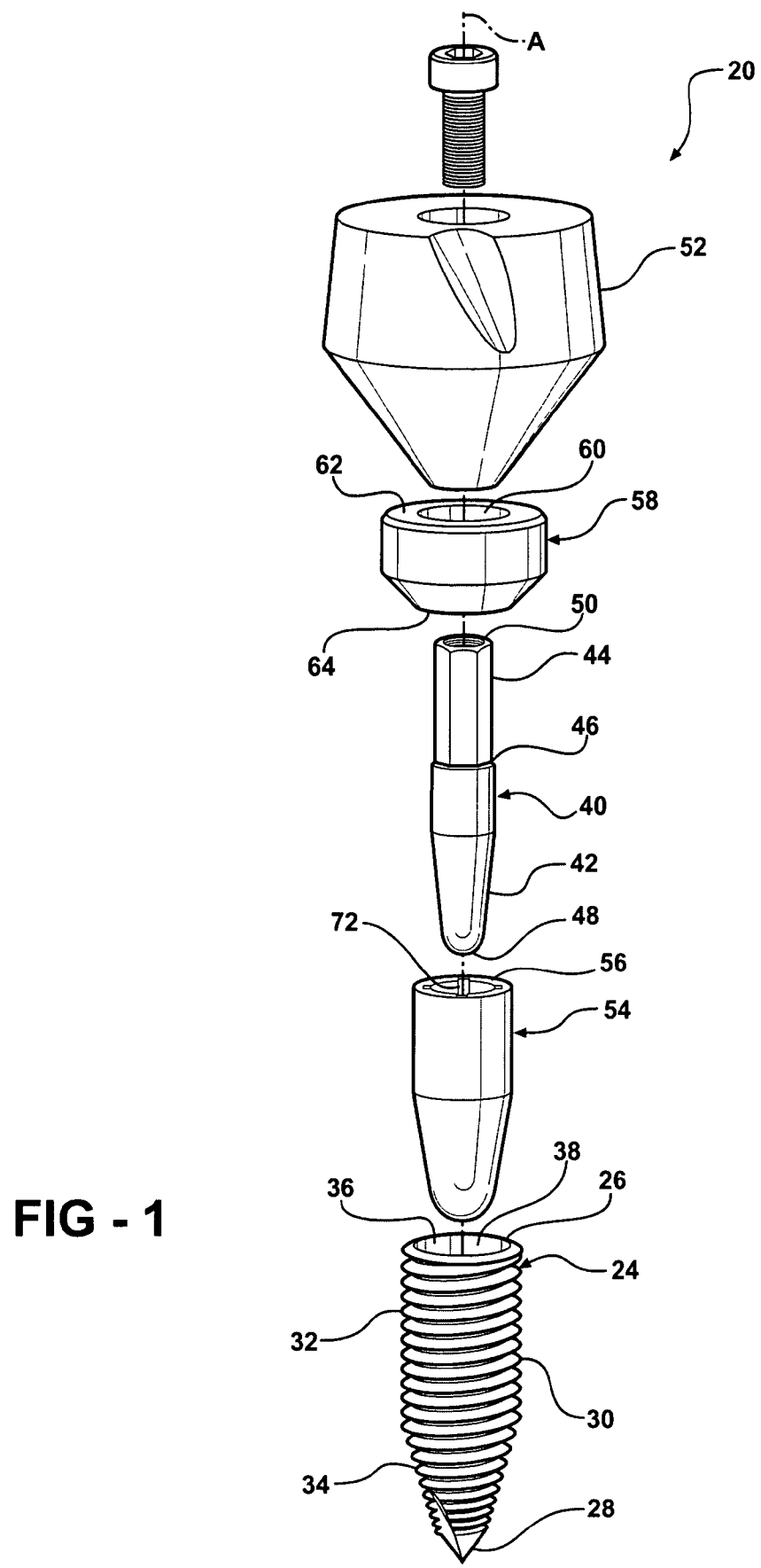
FIG. 1 is an exploded perspective view of the force distributing dental implant assembly.
Figure 2:
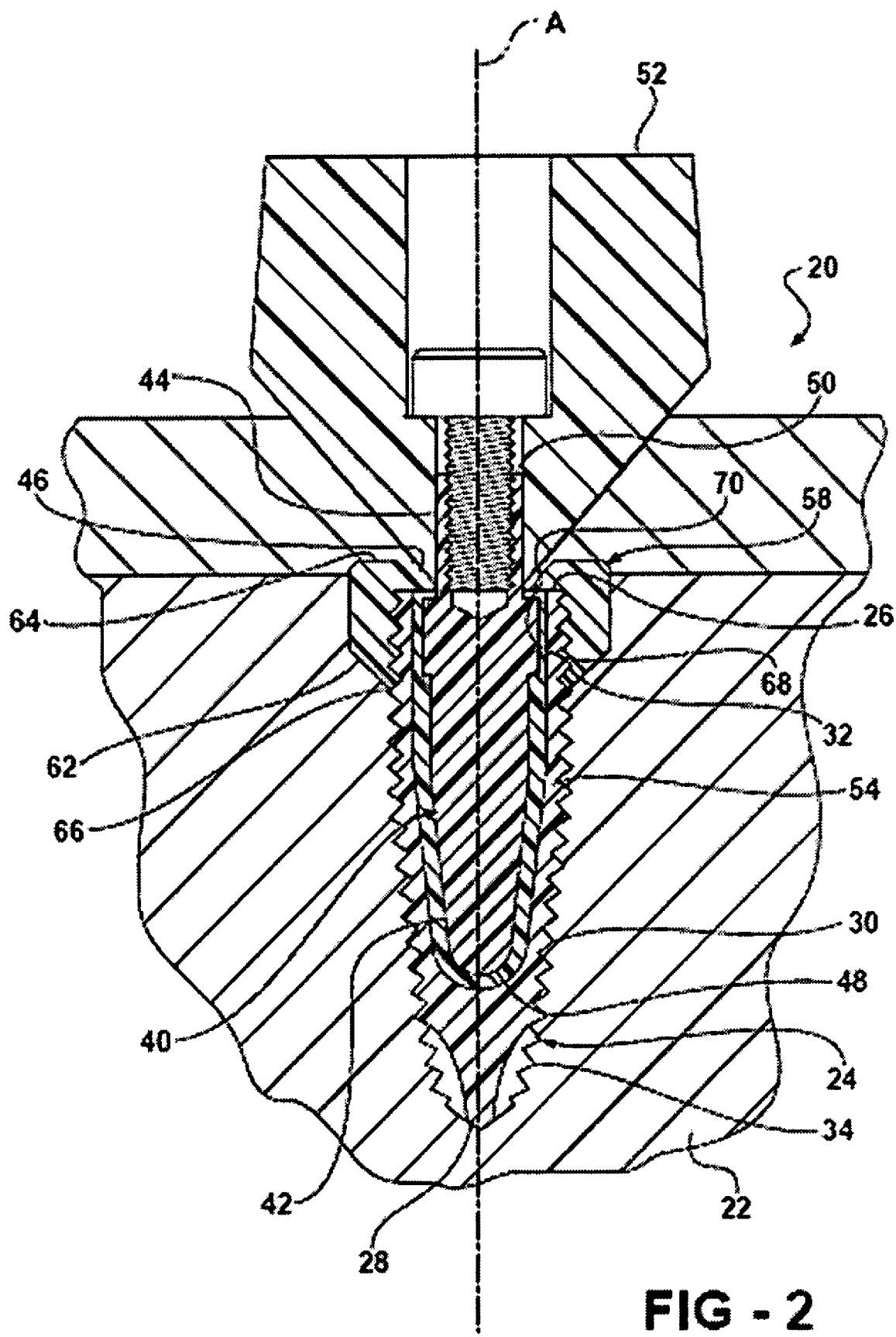
FIG. 2 is a sectional side view of the dental implant assembly in an installed state.

Referring to the Figures, wherein like numerals indicate corresponding parts throughout the several views, a first embodiment of a dental implant assembly 20 for attachment to a bone 22 of a person is generally shown in FIG. 1.

The assembly includes an anchor body 24, 124, 224, 424 having a circular cross-section decreasing in size along an axis A from an anchor top end 26, 126, 226, 426, or an open top end, to an anchor bottom end 28, 128, 228, 428. The anchor body 24, 124, 224, 424 has an outer attachment surface 30, 130, 230, 430 defining self-tapping threads in an upper section 32, 132, 232, 432 and a lower section 34, 134, 234, 434 for attachment to the bone 22. The outer attachment surface 30, 130, 230, 430 of the anchor body 24, 124, 224, 424 could also be smooth or vented.

The anchor body 24, 124, 224, 424 also includes an inner wall 36, 136, 236, 436 defining an anchor pocket 38, 138, 238, 438 having a circular cross-section decreasing in size from the anchor top end 26, 126, 226, 426 to an anchor pocket bottom, and the anchor pocket 38, 138, 238, 438 defines an inner attachment surface.

The anchor body 24, 124, 224, 424 could be made of any suitable material or combination of materials for supporting the dental implant assembly 20 in the bone 22 including titanium and various polymeric materials, e.g. polyetheretherketone (PEEK). The anchor body 24, 124, 224, 424 could also be coated with a bone 22 growth stimulant such as hydroxyapatite (HA).

A core body 40, 140, 240, 340, 440 has a core bottom 42, 142, 242, 342, 442 and a smaller core top 44, 144, 244, 344, 444 to define a shoulder 46, 146, 246, 346, 446, or a collar, therebetween. The core bottom 42, 142, 242, 342, 442 is disposed in the anchor pocket 38, 138, 238, 438 and has a circular cross-section decreasing in size from the shoulder 46, 146, 246, 346, 446 to a core bottom end 48, 148, 248, 348, 448. When the dental implant assembly 20 is installed in the patient's bone 22, the shoulder 46, 146, 246, 346, 446 of the core body 40, 140, 240, 340, 440 is positioned slightly below the anchor top end 26, 126, 226, 426. In the preferred embodiment, the core top 44, 144, 244, 344, 444 has a shaped cross-section for engaging a tooth-replicating device 52 to prevent rotation therebetween. The core top 44, 144, 244, 344, 444 extends from the shoulder 46, 146, 246, 346, 446 to a core top end 50, 150, 250, 350, 450.

The core body 40, 140, 240, 340, 440 could be made of any suitable material or combination of materials for supporting the tooth-replicating device 52 and transferring forces to the anchor including titanium, chrome cobalt, and various polymeric materials, e.g. PEEK.

A resilient adhesive layer 54, 154, 254, 354, 454 is disposed in the anchor pocket 38, 138, 238, 438 between the inner wall 36, 136, 236, 436 of the anchor body 24, 124, 224, 424 and the core bottom 42, 142, 242, 342, 442. The resilient adhesive layer 54, 154, 254, 354, 454 defines a flange 56 extending radially inward and above the shoulder 46, 146, 246, 346, 446 of the core body 40, 140, 240, 340, 440. When the dental implant assembly 20 is installed in the patient's bone 22, the top of the flange 56 is disposed slightly above or flush with the anchor top end 26, 126, 226, 426.

The resilient adhesive layer 54, 154, 254, 354, 454 allows the core body 40, 140, 240, 340, 440 to resiliently move relative to the anchor body 24, 124, 224, 424 for protecting the anchor body 24, 124, 224, 424 and bone 22 from violent shocks. The resilient adhesive layer 54, 154, 254, 354, 454 improves the durability and life of the dental implant assembly 20. The resilient adhesive member 54, 154, 254, 354, 454 may be made of any suitable material for absorbing the energy from the impact force on the core body 40, 140, 240, 340, 440 and transferring that force to the anchor body 24, 124, 224, 424 including rubber, nylon, Polyoxymethylene—Delrin, LLDPE, and polyurethane.

The assembly includes a screw cap body 58, or retaining member, defining an inner bore 60 being threadedly engaged to the self-tapping threads of the upper section 32, 132, 232, 432 of the outer attachment surface 30, 130, 230, 430 of the anchor body 24, 124, 224, 424. The screw cap body 58 defines an outer screw cap surface 62 extending radially from the inner bore 60 of the screw cap body 58. The outer screw cap surface 62 has a circular cross-section decreasing in size from a screw cap top end 64 to a screw cap bottom end 66 to define a conical shape. The conical shape of the screw cap outer attachment surface 30, 130, 230, 430 allows the screw cap body 58 to better engage the bone 22 and support the dental implant assembly 20.

The screw cap inner bore 60 defines a clamp 68, or a flange, extending radially inward and over the flange 56 of the resilient adhesive layer 54, 154, 254, 354, 454 and the shoulder 46, 146, 246, 346, 446 of the core body 40, 140, 240, 340, 440. When the screw cap body 58 is threadedly engaged to the self-tapping threads of the upper section 32, 132, 232, 432 of the outer attachment surface 30, 130, 230, 430 of the anchor body 24, 124, 224, 424, the clamp 68 presses down on the flange 56 of the resilient adhesive layer 54, 154, 254, 354, 454, which thereby applies pressure to the shoulder 46, 146, 246, 346, 446 of the core body 40, 140, 240, 340, 440 to hold the core bottom 42, 142, 242, 342, 442 in the anchor pocket 38, 138, 238, 438. The clamp 68 does not touch the core body 40, 140, 240, 340, 440.

The screw cap body 58 defines an upper screw cap aperture 70 having a circular cross-section decreasing in size from the screw cap top end 64 to the clamp 68 for defining a tapered hole to hold the tooth-replicating device 52.

The core bottom 42, 142, 242, 342, 442 engages the anchor body 24, 124, 224, 424 defining an anti-rotation mechanism for preventing the core body 40, 140, 240, 340, 440 from rotating about the axis A. Exemplary embodiments of the anti-rotation mechanism are shown in FIGS. 3-5.

Figure 3:
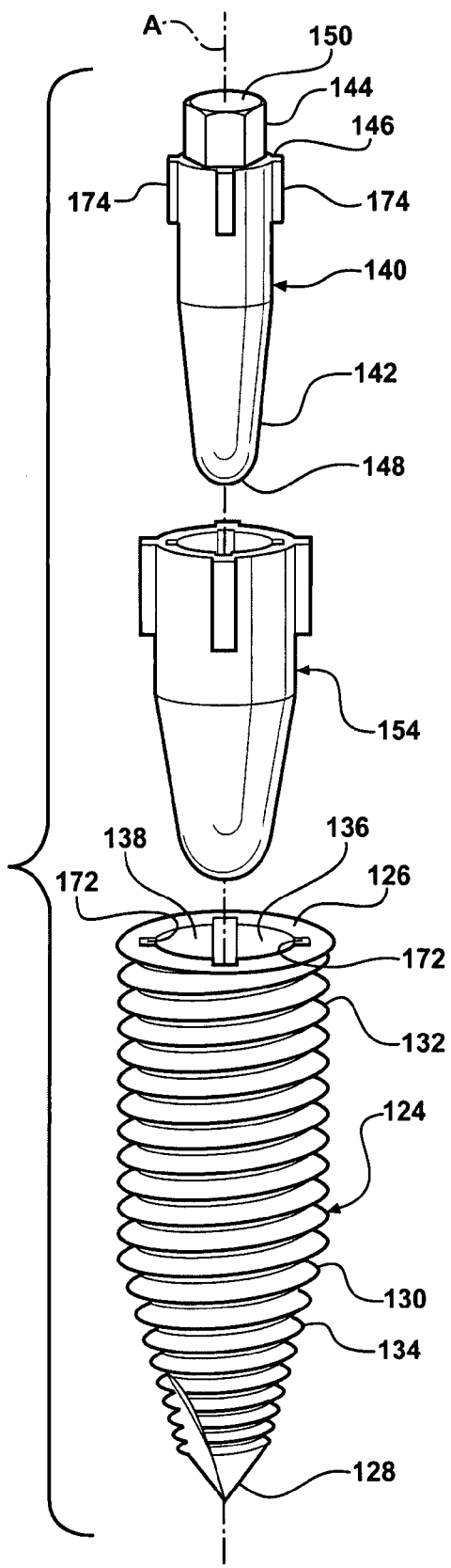
FIG. 3 is an exploded perspective view a second embodiment of the core body and the resilient adhesive layer and the anchor body.

Second embodiments of the core body 140 and the resilient adhesive layer 154 and the anchor body 124 are generally indicated in FIG. 3. The anchor body 124 defines a plurality of troughs 172 disposed about the anchor pocket 138 and extending axially along the anchor pocket 138. The core bottom 142 defines a plurality of protrusions 174 corresponding with the troughs 172 of the anchor pocket 138. The protrusions 174 extend radially into and engage the troughs 172 for preventing the core body 140 from rotating about the axis A.

Alternately, the protrusions 174 could be disposed on a separate ring member to be inserted over the core body 140.

Figure 4:
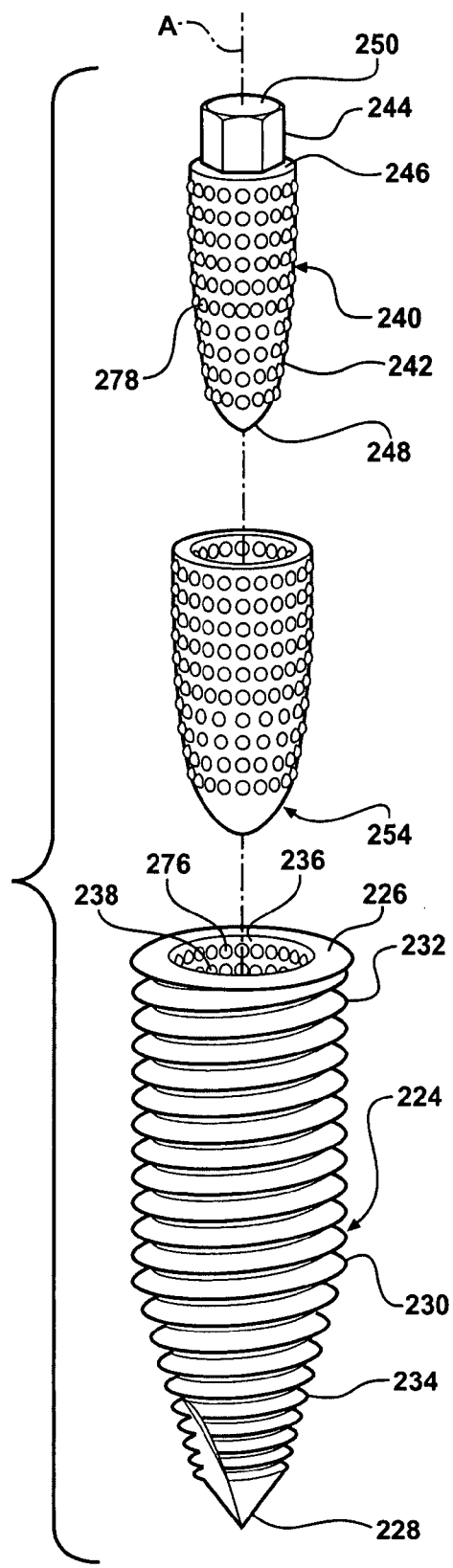
FIG. 4 is an exploded perspective view of a third embodiment of the core body and the resilient adhesive layer and the anchor body.
Figure 5:
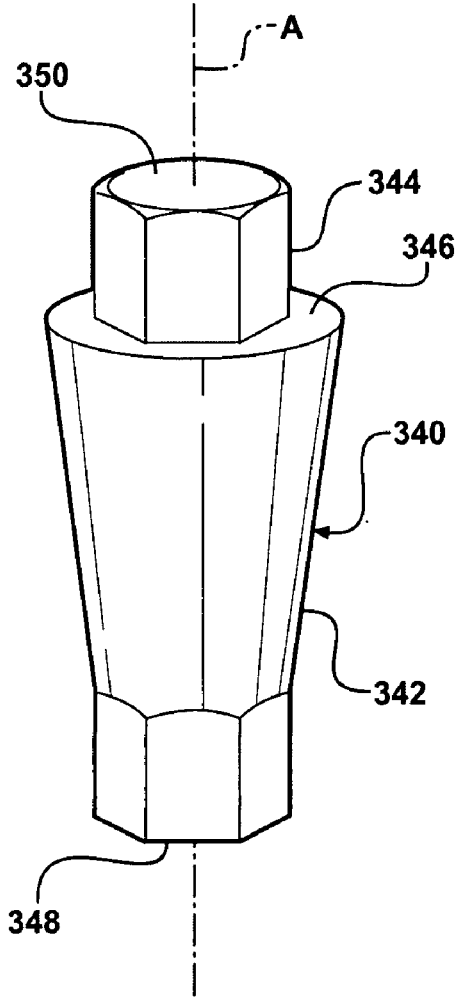
FIG. 5 is an exploded perspective view of a fourth embodiment of the core body and the resilient adhesive layer and the anchor body.

Third embodiments of the core body 240 and the resilient adhesive layer 254 and the anchor body 224 are generally indicated in FIG. 4. The inner wall 236 of the anchor pocket 238 defines a plurality of dimple recessions 276. The core bottom 242 defines a plurality of dimple protrusions 278 corresponding to the dimple recessions 276 of the anchor pocket 238. The dimple protrusions 278 of the core bottom 242 extend into and engage the dimple recessions 276 for preventing the core body 240 from rotating about the axis A.

A fourth embodiment of the core body 340 is generally indicated in FIG. 5. The anchor pocket bottom defines a receiving cavity having a hexagonal shaped cross-section. The core bottom end 348 has the same cross-section as the receiving cavity of the anchor pocket bottom. The core bottom end 348 extends into and engages the receiving cavity for preventing the core body 340 from rotating about the axis A. The core bottom end 348 and receiving cavity may have any cross-section suitable to prevent rotation therebetween.

Figure 6:
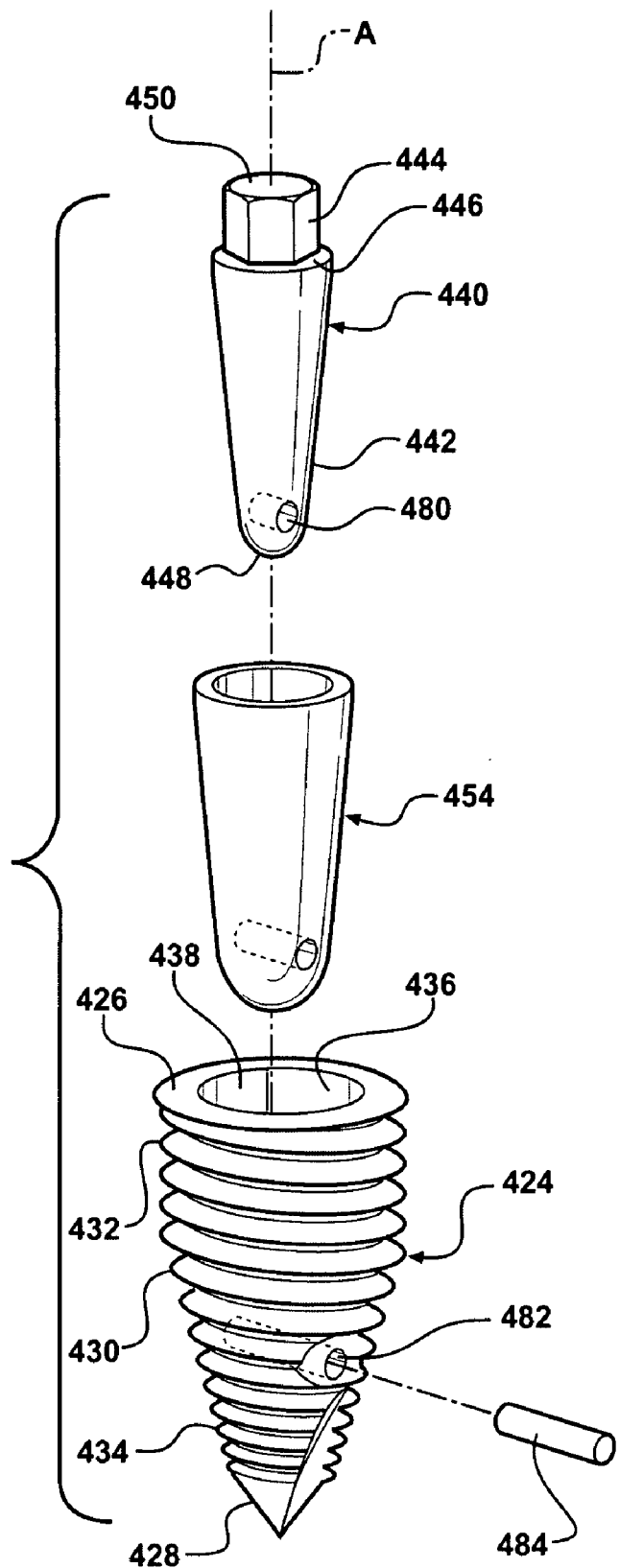
FIG. 6 is an exploded perspective view of a fifth embodiment of the core body and the resilient adhesive layer and the anchor body.

Fifth embodiments of the core body 440 and the resilient adhesive layer 454 and the anchor body 424 are generally indicated in FIG. 6. The core bottom 442 defines a passage 480 extending across the core bottom 442 and having a circular cross-section. The anchor body 424 defines two opposing anchor apertures 482 having the same cross-section as the passage 480 of the core bottom 442. A pin 484 is disposed through the anchor apertures 482 and the passage 480 of the core bottom 442 for preventing the core body 440 from rotating about the axis A.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. A dental implant assembly (20) that can be attached to a bone (22) of a person comprising:
   an anchor body (24, 124, 224, 424) having an outer attachment surface (30, 130, 230, 430) defining an upper section (32, 132, 232, 432) and a lower section (34, 134, 234, 434) for engaging the bone (22),
   said anchor body (24, 124, 224, 424) having an inner wall (36, 136, 236, 436) defining an anchor pocket (38, 138, 238, 438),
   a core body (40, 140, 240, 340, 440) including a core bottom (42, 142, 242, 342, 442) being disposed in said anchor pocket (38, 138, 238, 438) and a core top (44, 144, 244, 344, 444) for engaging a tooth-replicating device (52),
   said core top (44, 144, 244, 344, 444) being smaller than said core bottom (42, 142, 242, 342, 442) to define a shoulder (46, 146, 246, 346, 446) therebetween, a resilient adhesive layer (54, 154, 254, 354, 454) disposed in said anchor pocket (38, 138, 238, 438) between said inner wall (36, 136, 236, 436) of said anchor body (24,

124, 224, 424) and said core bottom (42, 142, 242, 342, 442) for allowing said core body (40, 140, 240, 340, 440) to move relative to said anchor body (24, 124, 224, 424), and characterized by said resilient adhesive layer (54, 154, 254, 354, 454) defining a flange (56) extending radially inward and above said shoulder (46, 146, 246, 346, 446) of said core body (40, 140, 240, 340, 440), and a screw cap body (58) disposed about said outer attachment surface (30, 130, 230, 430) of said anchor body (24, 124, 224, 424) and engaging said flange (56) of said resilient adhesive layer (54, 154, 254, 354, 454) and said shoulder (46, 146, 246, 346, 446) of said core body (40 140, 240, 340, 440) for holding said core body (40, 140, 240, 340, 440) and said anchor body (24, 124, 224, 424) and said resilient adhesive layer (54, 154, 254, 354, 454) together and for engaging the bone (22).

2. An assembly as set forth in claim 1 wherein said screw cap body (58) defines a clamp (68) extending radially inward over and engaging said flange (56) of said resilient adhesive layer (54, 154, 254, 354, 454) and said shoulder (46, 146, 246, 346, 446) of said core body (40, 140, 240, 340, 440) for holding said core body (40, 140, 240, 340, 440) and said resilient adhesive layer (54, 154, 254, 354, 454) and said anchor body (24, 124, 224, 424) together.

3. An assembly as set forth in claim 2 wherein said outer attachment surface (30, 130, 230, 430) of said anchor body (24, 124, 224, 424) defines self-tapping threads.

4. An assembly as set forth in claim 3 wherein said screw cap body (58) defines an inner bore (60) threadedly engaging said self-tapping threads of said upper section (32, 132, 232, 432) of said outer attachment surface (30, 130, 230, 430) of said anchor body (24, 124, 224, 424).

5. An assembly as set forth in claim 4 wherein said screw cap body (58) defines an upper screw cap aperture (70) having a circular cross-section decreasing in size from said screw cap top end (64) to said clamp (68) for defining a tapered hole to hold the tooth-replicating device (52).

6. An assembly as set forth in claim 1 wherein said screw cap body (58) defines an outer screw cap surface (62) having a circular cross-section decreasing in size from a screw cap top end (64) to a screw cap bottom end (66) of engaging the bone (22).

7. An assembly as set forth in claim 1 wherein said anchor body (24, 124, 224, 424) has a circular cross-section decreasing in size along an axis (A) from an anchor top end (26, 126, 226, 426) to an anchor bottom end (28, 128, 228, 428).

8. An assembly as set forth in claim 7 wherein said anchor pocket (38, 138, 238, 438) has a circular cross-section decreasing in size from said anchor top end (26, 126, 226, 426) to an anchor pocket (38, 138, 238, 438) bottom.

9. An assembly as set forth in claim 1 further including said core bottom (42, 142, 242, 342, 442) engaging said anchor body (24, 124, 224, 424) for preventing said core body (40, 140, 240, 340, 440) from rotating relative to said anchor body (24, 124, 224, 424).

10. An assembly as set forth in claim 9 wherein said anchor body (24, 124, 224, 424) further defines a plurality of troughs (172) disposed about said anchor pocket (38, 138, 238, 438), and said core bottom (42, 142, 242, 342, 442) defines a plurality of protrusions (174) extending radially into said troughs (172) of said anchor pocket (38, 138, 238, 438) for preventing said core body (40, 140, 240, 340, 440) from rotating relative to said anchor body (24, 124, 224, 424).

11. An assembly as set forth in claim 9 wherein said inner wall (36, 136, 236, 436) of said anchor pocket (38, 138, 238, 438) defines a plurality of dimple recessions (276), and said core bottom (42, 142, 242, 342, 442) defines a plurality of dimple protrusions (278) disposed about said core bottom (42, 142, 242, 342, 442) and engaging said dimple recessions (276) of said anchor pocket (38, 138, 238, 438) for preventing said core body (40, 140, 240, 340, 440) from rotating relative to said anchor body (24, 124, 224, 424).

12. An assembly as set forth in claim 9 wherein said anchor pocket (38, 138, 238, 438) extends along an axis (A) from an anchor top end (26, 126, 226, 426) to an anchor pocket (38, 138, 238, 438) bottom, said anchor pocket (38, 138, 238, 438) bottom defines a receiving cavity having a hexagonal shaped cross-section, said core bottom (42, 142, 242, 342, 442) extends axially from said shoulder (46, 146, 246, 346, 446) to a core bottom end (48, 148, 248, 348, 448) having the same cross-section as said receiving cavity of said anchor pocket (38, 138, 238, 438) bottom, and said hexagonal shaped core bottom end (48, 148, 248, 348, 448) engages said receiving cavity of said anchor pocket (38, 138, 238, 438) for preventing said core body (40, 140, 240, 340, 440) from rotating relative to said anchor body (24, 124, 224, 424).

13. An assembly as set forth in claim 9 wherein said core bottom (42, 142, 242, 342, 442) defines a passage (480) extending across said core bottom (42, 142, 242, 342, 442) and having a circular cross-section, said anchor body (24, 124, 224, 424) defines two opposing anchor apertures (482) having the same cross-section as said passage (480) of said core bottom (42, 142, 242, 342, 442), and a pin (484) is disposed through said anchor apertures (482) of said anchor body (24, 124, 224, 424) and said passage (480) of said core bottom (42, 142, 242, 342, 442) for preventing said core body (40, 140, 240, 340, 440) from rotating relative to said anchor body (24, 124, 224, 424).

14. A dental implant assembly (20) that can be attached to a bone (22) of a person comprising:

an anchor body (24, 124, 224, 424) being of titanium and having a circular cross-section decreasing in size along an axis (A) from an anchor top end (26, 126, 226, 426) to an anchor bottom end (28, 128, 228, 428), said anchor body (24, 124, 224, 424) having an outer attachment surface (30, 130, 230, 430) for attachment to the bone (22), said outer attachment surface (30, 130, 230, 430) of said anchor body (24, 124, 224, 424) defining self-tapping threads defining an upper section (32, 132, 232, 432) and a lower section (34, 134, 234, 434) for threading into the bone (22), said anchor body (24, 124, 224, 424) having an inner wall (36, 136, 236, 436) defining an anchor pocket (38, 138, 238, 438) having a circular cross-section decreasing in size from said anchor top end (26, 126, 226, 426) to an anchor pocket (38, 138, 238, 438) bottom, a core body (40, 140, 240, 340, 440) being of titanium, said core body (40, 140, 240, 340, 440) including a core bottom (42, 142, 242, 342, 442) and a smaller core top (44, 144, 244, 344, 444) to define a shoulder (46, 146, 246, 346, 446) therebetween, said core bottom (42, 142, 242, 342, 442) being disposed in said anchor pocket (38, 138, 238, 438) and having a circular cross-section decreasing in size from said shoulder (46, 146, 246, 346, 446) to a core bottom end (48, 148, 248, 348, 448), said shoulder (46, 146, 246, 346, 446) of said core body (40, 140, 240, 340, 440) being positioned below said anchor top end (26, 126, 226, 426), said core top (44, 144, 244, 344, 444) having a hexagonal shaped cross-section and extending from said shoulder (46, 146, 246, 346, 446) to a core top end (50, 150, 250, 350, 450) for engaging a tooth-replicating device (52), said core bottom (42, 142, 242, 342, 442) engaging said anchor body (24, 124, 224, 424) for preventing said core body (40, 140, 240, 340, 440) from rotating about said axis (A), a resilient adhesive layer (54, 154, 254, 354, 454) being of rubber and disposed in said anchor pocket (38, 138, 238, 438) between said inner wall (36, 136, 236, 436) of said anchor body (24, 124, 224, 424) and said core bottom (42, 142, 242, 342, 442) for allowing said core body (40, 140, 240, 340, 440) to move relative to said anchor body (24, 124, 224, 424), said resilient adhesive layer (54, 154, 254, 354, 454) defining a flange (56) extending radially inward and above said shoulder (46, 146, 246, 346, 446) of said core body (40, 140, 240, 340, 440) and being disposed adjacent to said anchor top end (26, 126, 226, 426), and characterized by a screw cap body (58) being of titanium defining an inner bore (60) threadedly engaging said self-tapping threads of said upper section (32, 132, 232, 432) of said outer attachment surface (30, 130, 230, 430) of said anchor body (24, 124, 224, 424), said screw cap body (58) defining an outer screw cap surface (62) extending radially of said inner bore (60) of said screw cap and having a circular cross-section decreasing in size from a screw cap top end (64) to a screw cap bottom end (66) for engaging the bone (22), said screw cap inner bore (60) defining a clamp (68) extending radially inward and over said flange (56) of said resilient adhesive layer (54, 154, 254, 354, 454) and said shoulder (46, 146, 246, 346, 446) of said core body (40, 140, 240, 340, 440) for holding said core body (40, 140, 240, 340, 440) and said anchor body (24, 124, 224, 424) and said resilient adhesive layer (54, 154, 254, 354, 454) together, said screw cap body (58) defining an upper screw cap aperture (70) having a circular cross-section decreasing in size from said screw cap top end (64) to said clamp (68) for defining a tapered hole to hold the tooth-replicating device (52).

15. An assembly as set forth in claim 14 wherein said anchor body (24, 124, 224, 424) further defines a plurality of troughs (172) disposed about said anchor pocket (38, 138, 238, 438) and extending axially along said anchor pocket (38, 138, 238, 438), and said core bottom (42, 142, 242, 342, 442) defines a plurality of protrusions (174) disposed about said core bottom (42, 142, 242, 342, 442) and extending radially into said troughs (172) of said anchor pocket (38, 138, 238, 438) for preventing said core body (40, 140, 240, 340, 440) from rotating about said axis (A).

16. An assembly as set forth in claim 14 wherein said inner wall (36, 136, 236, 436) of said anchor pocket (38, 138, 238, 438) defines a plurality of dimple recessions (276), and said core bottom (42, 142, 242, 342, 442) defines a plurality of dimple protrusions (278) disposed about said core bottom (42, 142, 242, 342, 442) and extending into said dimple recessions (276) of said anchor pocket (38, 138, 238, 438) for preventing said core body (40, 140, 240, 340, 440) from rotating about said axis (A).

17. An assembly as set forth in claim 14 wherein said anchor pocket (38, 138, 238, 438) bottom defines a receiving cavity having a hexagonal shaped cross-section, and said core bottom end (48, 148, 248, 348, 448) has the same cross-section as said receiving cavity of said anchor pocket (38, 138, 238, 438) bottom and extends into said receiving cavity for preventing said core body (40, 140, 240, 340, 440) from rotating about said axis (A).

18. An assembly as set forth in claim 14 wherein said core bottom (42, 142, 242, 342, 442) defines a passage (480) extending across said core bottom (42, 142, 242, 342, 442) and having a circular cross-section, said anchor body (24, 124, 224, 424) defines two opposing anchor apertures (482) having the same cross-section as said passage (480) of said core bottom (42, 142, 242, 342, 442) and extending from said outer attachment surface (30, 130, 230, 430) to said anchor pocket (38, 138, 238, 438), and a pin (484) is disposed through said anchor apertures (482) of said anchor body (24, 124, 224, 424) and said passage (480) of said core bottom (42, 142, 242, 342, 442) for preventing said core body (40, 140, 240, 340, 440) from rotating about said axis (A).

* * * * *